(12) United States Patent
Maesen et al.

(10) Patent No.: US 8,652,447 B2
(45) Date of Patent: *Feb. 18, 2014

(54) COSMETIC AND PERSONAL CARE PRODUCTS CONTAINING SYNTHETIC MAGNESIUM ALUMINO-SILICATE CLAYS

(75) Inventors: Theodorus Maesen, Point Richmond, CA (US); Alexander E. Kuperman, Orinda, CA (US); Ibrahim J. Uckung, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 976 days.

This patent is subject to a terminal disclaimer.

(21) Appl. No.: 12/337,892

(22) Filed: Dec. 18, 2008

(65) Prior Publication Data

US 2010/0158825 A1  Jun. 24, 2010

(51) Int. Cl.
| | | |
|---|---|---|
| A61K 8/26 | (2006.01) | |
| A61Q 15/00 | (2006.01) | |
| A61Q 19/00 | (2006.01) | |
| C01B 33/40 | (2006.01) | |
| C01B 33/26 | (2006.01) | |
| C01B 33/44 | (2006.01) | |
| C01B 33/46 | (2006.01) | |

(52) U.S. Cl.
CPC . *A61K 8/26* (2013.01); *A61Q 15/00* (2013.01); *A61Q 19/00* (2013.01); *C01B 33/40* (2013.01); *C01B 33/44* (2013.01); *C01B 33/46* (2013.01)
USPC ................. 424/59; 424/63; 424/68; 424/69; 423/328.1

(58) Field of Classification Search
CPC ......... A61K 8/26; A61Q 15/00; A61Q 19/00; C01B 33/40; C01B 33/46; C01B 33/26
USPC ....................... 424/59, 69, 63, 68; 423/328.1
See application file for complete search history.

(56) References Cited

U.S. PATENT DOCUMENTS

| | | | |
|---|---|---|---|
| 3,586,478 A | 6/1971 | Neumann | |
| 3,652,457 A | 3/1972 | Jaffe | |
| 3,666,407 A | 5/1972 | Orlemann | |
| 3,671,190 A | 6/1972 | Neumann | |
| 3,779,933 A | 12/1973 | Eisen | |
| 3,803,026 A | 4/1974 | Jaffe | |
| 3,844,978 A | 10/1974 | Hickson | |
| 3,844,979 A | 10/1974 | Hickson | |
| 3,887,692 A | 6/1975 | Gilman | |
| 3,892,655 A | 7/1975 | Hickson | |
| 3,904,741 A | 9/1975 | Jones et al. | |
| 3,887,454 A | 6/1976 | Hickson | |
| 4,049,780 A | 9/1977 | Neumann | |
| 4,515,633 A | 5/1985 | Cruz, Jr. | |
| 4,557,916 A | 12/1985 | Withiam | |
| 4,569,923 A | 2/1986 | Knudson et al. | |
| 4,664,842 A | 5/1987 | Knudson et al. | |
| 4,743,305 A | 5/1988 | Doidge et al. | |
| 4,844,790 A | 7/1989 | Occelli | |
| 5,075,033 A | 12/1991 | Cody et al. | |
| 5,110,501 A | 5/1992 | Knudson et al. | |
| 5,160,454 A | 11/1992 | Knudson et al. | |
| 5,164,433 A | 11/1992 | Ricci et al. | |
| 5,358,562 A | 10/1994 | Nae et al. | |
| 5,407,477 A | 4/1995 | Reynolds et al. | |
| 5,498,285 A | 3/1996 | Hooykaas | |
| 5,525,330 A | 6/1996 | Gaffar et al. | |
| 5,634,969 A | 6/1997 | Cody et al. | |
| 5,798,324 A | 8/1998 | Svoboda | |
| 5,885,599 A | 3/1999 | Peterson et al. | |
| 5,919,312 A | 7/1999 | Wierenga et al. | |
| 5,981,625 A | 11/1999 | Zou et al. | |
| 6,187,710 B1 | 2/2001 | Vogels et al. | |
| 6,303,531 B1 | 10/2001 | Lussier et al. | |
| 6,334,947 B1 | 1/2002 | De Boer et al. | |
| 6,451,200 B1 | 9/2002 | Lussier et al. | |
| 6,565,643 B2 | 5/2003 | Nieman et al. | |
| 6,716,337 B2 | 4/2004 | Nieman et al. | |
| 6,716,418 B2 | 4/2004 | SenGupta et al. | |
| 6,716,785 B2 | 4/2004 | Stamires et al. | |
| 6,890,502 B2 | 5/2005 | Bauer et al. | |
| 7,163,669 B2 | 1/2007 | Withiam et al. | |
| 7,303,767 B2 | 12/2007 | Withiam et al. | |
| 2001/0036435 A1 | 11/2001 | Nieman et al. | |
| 2004/0062681 A1 | 4/2004 | Winston | |

OTHER PUBLICATIONS

U.S. Appl. No. 12/245,548, "Hydrocracking Catalyst and Process Using a Magnesium Aluminosilicate Clay," Filed Oct. 3, 2008, Maesen et al.
U.S. Appl. No. 12/245,531, "Hydrodemetallization Catalyst and Process," Filed Oct. 3, 2008, Dillion et al.
U.S. Appl. No. 12/245,414, "Magnesium Aluminosilicate Clays-Synthesis and Catalysis," Filed Oct. 3, 2008, Kuperman et al.
PCT/US2009/066808 filed Dec. 4, 2009, PCT International Search Report, Mail dated May 31, 2010.

*Primary Examiner* — Mina Haghighatian
(74) *Attorney, Agent, or Firm* — Chloe Zubieta; E. Joseph Gess; Michael D. Ross

(57) ABSTRACT

The invention provides for cosmetic and personal care compositions comprising a synthetic magnesium aluminosilicate clay. The synthetic magnesium aluminosilicate clay is formed at ambient pressure by a series of reaction steps and a pH change from acidic pH to basic pH. The characteristics of the magnesium aluminosilicate clay, including platelet size, degree of stacking, and porosity can be tuned depending on the cosmetic or personal care product desired. In addition, these cosmetic and personal care compositions optionally include one or more of the following components: odor controlling agents, skin protectants, diluents, lipophilic skin health benefit agents, sunscreens, humectants, emollients, slip compounds, and moisturizers.

18 Claims, No Drawings

COSMETIC AND PERSONAL CARE PRODUCTS CONTAINING SYNTHETIC MAGNESIUM ALUMINO-SILICATE CLAYS

FIELD OF THE INVENTION

This invention is directed to compositions comprising synthetic magnesium aluminosilicate clays and methods of making and using said compositions.

BACKGROUND OF THE INVENTION

A broad array of homecare, topical personal care, cosmetic, pharmaceutical, and personal hygiene products are available. These products include cleaners, odor absorbers, sports and athletic sprays and powders, antiperspirants, foot and body powders, body sprays, and deodorants. Other types of products are available to absorb sebum oils and residues generated by the sebaceous glands within a person's skin. Products of these types are widespread within the home and personal care industries and the search for new and effective additives for such purposes has existed for many years.

Clays, for example, have been used to absorb odors and perspiration. The physical properties of the clay such as platelet size and degree of platelet stacking in part determine the effectiveness of the clay given the application. Unlike heavily perfumed products that mask odors and can lead to skin irritations, clays are generally non-irritating to the skin. However, most naturally occurring clay minerals may be in an impure state and the complete purification of some may be difficult and expensive. Common contaminants found in naturally occurring clay minerals may include arsenic, lead, chromium, and titanium. Thus, it may be desirable to manufacture synthetic clay-like materials in substantially purer forms with commercially economic yields. Commercial synthetic routes to clays can involve hydrothermal synthesis and/or multiple reaction steps which can increase the cost of synthetic clays relative to the naturally occurring materials. Thus, there exists a need for inexpensive synthetic clays with appropriate physical properties for use in cosmetics, personal care products, and other applications. Layered magnesium aluminosilicates can be described as a type of clay comprising alternating layers of octahedrally co-ordinated magnesium atoms and tetrahedrally co-ordinated silicon and/or aluminum atoms. Magnesium aluminosilicate clays have a negative layer charge which can be balanced by cations. The type of charge balancing cations can affect the characteristics of the magnesium aluminosilicate clays. Among other uses, clays such as magnesium aluminosilicates, can be used in cosmetics or personal care products due to their physical properties such as odor and oil absorbance. Examples of further applications in which layered magnesium aluminosilicates may be used include, but are not limited to, coatings, inks, greases, home-care products, nanocomposites, drilling fluids, pharmaceuticals, catalysis, purification methodologies, or ion-exchange applications.

Depending on the intended use, it may be desirable to provide control over the morphology, size, crystallinity, and/or charge of synthetic magnesium aluminosilicates. It may be desirable to economically produce a material that exhibits improved performance in various applications. It may also be of interest to manufacture synthetic magnesium aluminosilicate clays having properties similar to or better than naturally occurring magnesium aluminosilicate clays. Such improved properties may include improved Theological control, purity, crystallinity, and morphology.

SUMMARY OF THE INVENTION

The present invention is directed to cosmetic, personal care, home care, and topical pharmaceutical compositions comprising synthetic magnesium aluminosilicate clays and methods of making and using said compositions. Specifically, the invention provides for a cosmetic composition comprising a magnesium aluminosilicate clay wherein said magnesium aluminosilicate clay is synthesized according to a method comprising the following steps:

a) combining (1) a silicon component, (2) an aluminum component, and (3) a magnesium component, under aqueous conditions at a first reaction temperature and at ambient pressure, to form a first reaction mixture, wherein the pH of said first reaction mixture is acidic;

b) adding an alkali base to the first reaction mixture to form a second reaction mixture wherein the pH of the second reaction mixture is greater than the pH of the first reaction mixture; and c) reacting the second reaction mixture at a second reaction temperature and for a time sufficient to form a product comprising a magnesium aluminosilicate clay.

In an embodiment, the cosmetic composition of the invention further comprises at least one skin aid selected from the group consisting of skin protectants, diluents, lipophilic skin health benefit agents, sunscreens, humectants, emollients, slip compounds, and moisturizers.

The invention also provides for a personal care composition comprising a magnesium aluminosilicate clay wherein said magnesium aluminosilicate clay is synthesized according to a method comprising the following steps:

a) combining (1) a silicon component, (2) an aluminum component, and (3) a magnesium component, under aqueous conditions at a first reaction temperature and at ambient pressure, to form a first reaction mixture, wherein the pH of said first reaction mixture is acidic;

b) adding an alkali base to the first reaction mixture to form a second reaction mixture wherein the pH of the second reaction mixture is greater than the pH of the first reaction mixture; and c) reacting the second reaction mixture at a second reaction temperature and for a time sufficient to form a product comprising a magnesium aluminosilicate clay.

In an embodiment, the personal care composition of the invention further comprises an odor controlling agent.

In an embodiment, the magnesium aluminosilicate clay used in the cosmetic composition or the personal care composition of the invention has a silicon to aluminum elemental mole ratio greater than 3 and the $^{29}$Si NMR of the magnesium aluminosilicate clay comprises peaks as given in Table 1:

TABLE 1

| Peaks | Chemical shift (ppm)[1] |
|---|---|
| P1 | −79 |
| P2 | −82 |
| P3 | −85 |
| P4 | −88 |
| P5 | −93 |

[1] +/−3 ppm

DETAILED DESCRIPTION

Embodiments are described herein which provide compositions comprising synthetic magnesium aluminosilicate clays. The synthetic magnesium aluminosilicate clays may have improved properties. Examples of improved properties include, but are not limited to, improved purity, crystallinity, morphology and/or Theological control. The synthetic magnesium aluminosilicate clays may be made such that a variety of charges, sizes, cation exchange capacity, surface area and/or morphologies may be altered and/or controlled.

DEFINITIONS

While the invention is susceptible to various modifications and alternative forms, specific embodiments thereof are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

The following terms will be used throughout the specification and will have the following meanings unless otherwise indicated.

By "personal care compositions" it is meant compositions that comprise at least one material (in addition to the inventive synthetic magnesium aluminosilicate clay) that is typically utilized for the treatment of a person's skin (such as, as examples, skin softeners, antiperspirant salts, cosmetics, absorbent materials, and the like). Types of such personal care compositions include, without limitation, either fluid or solid in nature, deodorants, antiperspirants, athletic sprays, body sprays, hair conditioners, shampoo, skin conditioners, body washes, liquid bath soaps, facial cleansers, make-up removers, baby baths, hand soaps, make-up foundation, skin-coloring formulations, sunscreens, and the like. Other articles such as diapers, adult incontinence products, training pants, and bath tissue are also examples of personal care compositions.

As used herein "pharmaceutical compositions" mean compositions that comprise at least one material (in addition to the inventive synthetic magnesium aluminosilicate clay) that is biologically active. The pharmaceutical composition will generally contain inert ingredients and one or more "active" or "biologically active" ingredients. By "active" or "biologically active" it is meant a compound or molecule that exerts a beneficial or adverse effect on living matter.

The present compositions may optionally comprise slip compounds. The term "slip compounds," as used herein, refers to compounds which have unique structures which provide enhanced slip/lubrication characteristics of powders and/or reduced skin to skin friction between intertriginous skin sites.

By "fluid composition" it is meant a composition that contains greater than 20% by weight of one or more ingredients acceptable for use in cosmetics that are liquid at temperatures less than 100° C., such as lotions, creams, gels, semisolids, emulsions, solutions, dispersions, foams, mousses, sprays and the like.

As used herein, the phrase "lipophilic skin health benefit agent" is defined as any substance that has a higher affinity for oil over water and provides a skin health benefit by directly interacting with the skin. Suitable examples of such benefits include, but are not limited to, enhancing skin barrier function, enhancing moisturization and nourishing the skin.

The term "mesoporous" refers to an average pore size of about 2 to 50 nm as described in IUPAC Appendix to the *Manual of Symbols and Terminology for Physicochemical Quantities and Units* (Butterworths: 1970 and *Pure and Applied Chemistry*, 1970, 21, No. 1)

The term "ambient pressure" refers to pressures in the range of about 0.9 bar to about 1.2 bar.

The BET surface area is determined by adsorption of nitrogen at 77K and mesopore surface area by the BJH method (described in E. P. Barrett, L. C. Joyner and P. H. Halenda, J. Amer. Chem. Soc., 73, 1951, 373). The micropore volume is determined by the DR equation (as described in Dubinin, M. M. Zaverina, E. D. and Raduskevich, L. V. Zh. Fiz. Khimii, 1351-1362, 1947). The total pore volume is determined from the nitrogen adsorption data, the mesopore volume is determined by the difference between total pore volume and the micropore volume.

The $^{29}$Si NMR spectra were collected at a spinning speed of 8 kHz with at least 500 scans and a relaxation time of 100 seconds between scans.

Silicon to aluminum elemental mole ratios of magnesium aluminosilicate clays can be determined from the $^{29}$Si NMR based on peak intensities. See, for example, G. Engelhardt and D. Michel (1987), *High-Resolution Solid-State NMR of Silicates and Zeolites*. New York: John Wiley & Sons, in particular pages 180-187.

The synthetic magnesium aluminosilicate clay employed in the present invention is synthesized according to specific reaction steps. Briefly, the synthesis of the magnesium aluminosilicate clay involves forming an aqueous mixture of a silicon component, an aluminum component, and a magnesium component under acidic conditions to form a first reaction mixture. As used herein "component" refers to any material, salt, and/or compound comprising a given element which can act as a source of said element. For example "silicon component" can refer to silicon in the elemental form, silicon containing compounds, and/or silicon salts which can be used as a source of silicon. Examples of silicon components useful in the process of the invention include, but are not limited to, sodium silicate, potassium silicate, silica gels, silica sols, and combinations thereof. Examples of aluminum components aluminum include, but are not limited to, sodium aluminate, potassium aluminate, aluminum sulfate, aluminum nitrate, and combinations thereof. Examples of magnesium components include, but are not limited to, magnesium metal, magnesium hydroxide, magnesium halides, magnesium sulfate, and magnesium nitrate.

In the first reaction mixture, the ratio of silicon to aluminum to magnesium, can be expressed in terms of elemental mole ratios as:

aSi:bAl:cMg wherein "a" has a value from 6 to 8, "b" has a value from 0.001 to 7.9, and "c" has a value of from 0.1 to 6, wherein b=(6−c)+(8−a), and wherein a:b is at least 3.

The silicon, aluminum, and magnesium components are combined, under aqueous conditions, to form a first reaction mixture wherein the first reaction mixture has an acidic pH. In one aspect the pH of the first reaction mixture is in the range of between about 0 to about 5. The pH of the first reaction mixture can be adjusted by the addition of an acid in order to achieve a pH of between about 0 to about 5. Examples of acids include, but are not limited to, mineral acids such as sulfuric acid, hydrochloric acid, and nitric acid. Organic acids such as acetic acid, citric acid, formic acid, and oxalic acid can also be used.

The first reaction mixture is generally formed under ambient pressure and temperature conditions. Pressures ranges for the reaction are between about 0.9 bar and 1.2 bar, preferably between about 1.0 bar and about 1.1 bar. The temperature for the formation of the first reaction mixture is not critical. The temperature can be between the freezing point and the boiling point of the first reaction mixture. Generally, the temperature is between about 0° C. and 100° C. and preferably at least 50° C.

After addition of the silicon, aluminum, and magnesium components and adjustment of the pH to an acidic range to form the first reaction mixture, an alkali base is added to form a second reaction mixture. Examples of alkali base include, but are not limited to, sodium hydroxide and potassium hydroxide. Sufficient alkali base is added to the first reaction mixture so as to ensure that the pH of the resulting second reaction mixture is at least 7.5.

The second reaction mixture is then reacted for sufficient time and at sufficient temperature to form the magnesium aluminosilicate clay that forms a component of the invention. In embodiments, the time is at least one second, preferably at least 15 minutes, and most preferably at least 30 minutes. In some embodiments, precipitation of the magnesium aluminosilicate clay used in the invention can be instantaneous. The temperature can be between the freezing point and the boiling point of the second reaction mixture. In embodiments, the temperature of the second reaction mixture can range from about 0° C. to about 100° C. In an embodiment, the temperature of the second reaction mixture is at least 50° C. Generally, higher temperatures result is shorter times to form the magnesium aluminosilicate clay. The reaction can be done at ambient pressure, although higher or lower pressures are not excluded. In the synthesis process described, the magnesium aluminosilicate clay is formed in the second reaction mixture step. In embodiments, the magnesium aluminosilicate clay used in the invention quantitatively precipitates from the second reaction mixture. The second reaction mixture, upon precipitation of the magnesium aluminosilicate clay comprises the solid magnesium aluminosilicate clay and a supernatant. By "supernatant" it is meant the aqueous portion of the reaction mixture that is in liquid form, essentially free of solid or particulate material. The magnesium aluminosilicate clay can be collected by, for example, filtration, evaporation of the supernatant, or centrifugation. The addition of an alkali base during the second step of the synthesis process will incorporate alkali cations into the magnesium aluminosilicate clay. The morphology and other characteristics of the magnesium aluminosilicate clay can be tailored to the desired application by controlling the reaction times, temperatures, and pH.

The magnesium aluminosilicate clay can be washed, and/or dried, and/or ion exchanged, and/or calcined. Depending on the end us, the magnesium aluminosilicate clay can be shaped according to processes known in the art.

The product of the above described process is a magnesium aluminosilicate clay. The ratio of silicon to aluminum in the magnesium aluminosilicate clay is at least 3. The ratio of silicon to aluminum to magnesium of the magnesium aluminosilicate clay can be expressed in terms of elemental mole ratios:

dSi:eAl:fMg wherein "d" has a value from 6 to 8, "e" has a value from 0.001 to 7.9, and "f" has a value of from 0.1 to 6, wherein e=(6−f)+(8−d), and wherein d:e is at least 3.

The magnesium aluminosilicate clay is a layered material composed of elemental clay platelets. The size of the clay platelets of the magnesium aluminosilicate clay is dependent on the reacting temperature and the reacting time of the second reaction mixture. Generally, the higher the temperature and the longer the time, the larger the clay platelets will be. Depending on the desired size of the clay platelets in the product, reacting time and temperature can be varied accordingly. In one embodiment of the present invention the product comprises clay platelets with an average size of from about 5 nm to about 500 nm in the longest dimension. In another embodiment the product comprises clay platelets with an average size of from about 5 nm to about 50 nm in the longest dimension.

The degree of stacking of the clay platelets is dependent on the ionic strength of the second reaction mixture. A high ionic strength will give much-stacked structures, while a low ionic strength will lead to structures exhibiting little stacking. The ionic strength of the second reaction mixture can be adjusted by increasing or decreasing the concentration of reactants (silicon, aluminum, and magnesium components) and altering the pH. For example, a dilute solution with a pH about 8 will have a lower ionic strength than a solution with a high concentration of reactants and a pH higher than 8. In one embodiment, the clay platelets have a degree of stacking of between 1 to about 5, in another embodiment the clay platelets have a degree of stacking of between about 1 to about 3. The lower limit is constituted by unstacked clay platelets, which have a "degree of stacking" of 1. The two parameters-the size of the clay platelets and the degree of stacking—can be estimated by means of transmission electron microscopy (TEM) and powder x-ray diffraction respectively. In an embodiment, the powder x-ray diffraction of the magnesium aluminosilicate clay of the invention has only broad peaks. Broad peaks are indicative of a low degree of stacking.

The individual clay platelets are composed of sheets of octahedrally coordinated metal ions interlinked by means of oxygen ions and sheets of tetrahedrally coordinated metal ions interlinked by oxygen ions. The apical oxygen atoms of the tetrahedral sheets help form the base of the octahedral sheets, thus connecting the sheets to one another. A regular assemblage of sheets (for example tetrahedral-octahedral or tetrahedral-octahedral-tetrahedral) is called a layer. If the sheet arrangement is tetrahedral-octahedral it is referred to as 1:1, if the sheet arrangement is tetrahedral-octahedral-tetrahedral it is referred to as 2:1. The magnesium aluminosilicate clay employed in the invention can be described as a 2:1 layered magnesium aluminosilicate clay.

The ion exchange capacity and absorption capabilities of the magnesium aluminosilicate clay stems in part from the charge on the sheets. A neutral tetrahedral sheet requires that the tetrahedrally co-ordinated metal ion have a tetravalent charge. In general, the metal ion will be $Si^{4+}$. To have a neutral octahedral layer, the metal ions present in that layer will have to provide a total charge of 6+ for every three octahedral cavities. This can be achieved by filling two out of every three octahedral cavities with trivalent metal ions, such as $Al^{3+}$, or by filling all octahedral cavities of each set of three with divalent metal ions, such as $Mg^{2+}$. This gives two types of octahedral layers, trioctahedral layers, in which all octahedral sites are filled and dioctahedral layers, which have two thirds of the octahedral sites filled. We believe that the product of the present invention comprises a 2:1 trioctahedral magnesium aluminosilicate. For further description of clay classification see J. Theo Kloprogge, Sridhar Komameni, and James E. Amonette, "Synthesis of smectite clay minerals; a critical review" *Clays and Clay Minerals*; October 1999; v. 47; no. 5; p. 529-554, herein incorporated by reference.

When lower valency cations are substituted or partially substituted for higher valency cations in the clay platelet structure, the clay platelet is negatively charged. For instance, in the tetrahedral layer trivalent metal ions, for example $Al^{+3}$, may be substituted for a portion of the tetravalent metal ions such as $Si^{+4}$. In the case of a clay with a trioctahedral layer structure, such as the product of the process of the present invention, such a substitution will give a saponite or a vermiculite. The divalent $Mg^{2+}$ metal ions in the octahedral layer can be substituted or partially substituted by monovalent metal ions such as $Na^+$, $K^+$, or $Li^+$.

Isomorphous substitution may occur only in the octahedral layer, only in the tetrahedral layer, or in both layers. In this context the term isomorphous substitution also refers to the removal of cations without the incorporation into the lattice of replacement cations, by which vacancies are produced. It will be clear that this removal also generates negative charges.

The neutral tetrahedral layer comprises $Si^{4+}$ ions. At least a portion of the $Si^{4+}$ ions can be substituted by trivalent ions to impart a negative charge on the layer. The trivalent ions in the tetrahedral layer preferably are aluminium ($Al^{3+}$) ions, although other trivalent ions such as chromium, cobalt (III), iron (III), manganese (III), titanium (III), gallium, vanadium, molybdenum, tungsten, indium, rhodium, and/or scandium can also be substituted. In an aspect of the invention, the magnesium aluminosilicate clay comprises at least 1 ppm $Al^{3+}$ ions. The neutral octahedral layer comprises divalent magnesium ($Mg^{2+}$) ions, although other divalent ions such as nickel, cobalt (II), iron (II), manganese (II), copper (II) and/or beryllium can also be incorporated into the neutral octahedral layer. The divalent ions of the neutral octahedral layer can be substituted by monovalent ions such as lithium ($Li^+$) ions to impart a negative charge on the octahedral layer.

The negative charge generated by isomorphous substitution is counterbalanced by the incorporation of cations, also known as counter-ions, into the space between the clay platelets. These counter-ions often are sodium or potassium. Generally, these cations are incorporated in the hydrated form, causing the clay to swell. For this reason, clays with negatively charged clay platelets are also known as swelling clays.

The magnesium aluminosilicate clay employed in the invention can be characterized by surface area and pore characteristics. The magnesium aluminosilicate clay employed in the invention generally has an average B.E.T. surface area in the range of 100 to 1000 $m^2/g$ and preferably in the range of 400 to 900 $m^2/g$. The magnesium aluminosilicate clay has an average pore volume, determined by means of B.E.T. nitrogen adsorption, in the range of 0.3 to 2.0 cc/g, preferably in the range of at least 0.5 cc/g, and most preferably in the range of at least 0.9 cc/g. The magnesium aluminosilicate clay has an average pore size, determined by means of nitrogen adsorption/desorption in the mesoporous range. In embodiments, the magnesium aluminosilicate clay of the present invention is mesoporous with an average pore size of about 2 nm to about 50 nm.

In an embodiment, the magnesium aluminosilicate clay employed in the invention has a silicon to aluminum elemental mole ratio greater than 3. The $^{29}Si$ NMR of the magnesium aluminosilicate clay comprises peaks as given in Table 1:

TABLE 1

| Peaks | Chemical shift (ppm)[1] |
|---|---|
| P1 | −79 |
| P2 | −82 |
| P3 | −85 |
| P4 | −88 |
| P5 | −93 |

[1] +/−3 ppm

Various post-synthesis procedures can be used to tailor the magnesium aluminosilicate clay physical characteristics to the desired final product composition. For example, the magnesium aluminosilicate clay may spray dried using known methods. A spray-dried magnesium aluminosilicate clay is free flowing, and is especially desirable in many applications. In a still further embodiment the magnesium aluminosilicate clay may be milled to produce a product of very fine particle size. Alternatively, the magnesium aluminosilicate clay may be beaded or pelletized by known methods to produce particles of any desired size.

Additionally, it is envisioned that using high shear techniques, such as ultrasonic and homogenizing equipment, may be used in certain embodiments. The shear may be applied during one or more of the reaction stages to influence the course of the reaction, the reaction rate, the products produced, and/or the features of the products produced. Shearing may be used, for example, at the end of the reaction to increase dispersion of the resulting clay. Further information about processing clays through homogenizing equipment may be found in U.S. Pat. Nos. 4,569,923; 4,664,842; 5,110,501; 5,160,454 all to Knudson, Jr. et al., and U.S. Pat. No. 4,743,305 to Doidge et al., all of which are incorporated herein by reference.

A post-synthesis treatment of the alkali substituted magnesium aluminosilicate clay is ion-exchange. For example, the clay platelets can be modified to produce what is known in the prior art as "organoclays" by treating them with quaternary surfactants that can adsorb on the clay-surface via ion exchange (for example, as described in U.S. Pat. Nos. 5,075,033, 5,164,433, 5,358,562, 5,407,477, and 5,634,969). For example, a surface-modifying reagent can be added to an aqueous clay-slurry and the resulting mixture can be agitated for a given period of time during which the reagent is allowed to "react" (e.g., ion-exchange) with the clay surface. After completion of the reaction, the slurry is filtered, and the filter cake dried and pulverized to produce the modified clay. In another method, the clay is extruded along with the surface-modifying reagent, followed by drying and pulverizing of the extruded material.

Personal care compositions of the invention comprise the magnesium aluminisilicate clay described above. In general, the magnesium aluminosilicate clay will be in a dispersion form within a cosmetic, deodorant, or other personal care formulation. In the compositions of the invention, the magnesium aluminosilicate clay described above can be used alone or in combination with other components. The cosmetic, personal care, and pharmaceutical compositions of the invention given below and are not intended to limit the scope of the invention but rather to provide examples of the invention.

Personal Care and Cosmetics Compositions

Examples of personal care and cosmetic compositions of the invention comprising the magnesium aluminosilicate clay described above may include skin-care creams, lotions, facial creams, and sunscreens; hair care products such as shampoos, conditioners, colorants, and hair styling aids; liquid makeups, foundations, shaving creams and lotions. The invention is also directed to topical pharmaceutical formulations comprising the magnesium aluminosilicate clay. The foregoing personal care, cosmetic, and pharmaceutical products can be in the form of oil-in-water emulsion or water-in-oil emulsion, solids, fluids, or gels.

The present invention provides novel compositions and absorbent products comprising the synthetic magnesium aluminosilicate described herein, to adsorb, or sequester bodily waste skin irritants, such as fecal enzymes, to provide skin health benefits.

Absorbent personal care articles, such a diapers and adult incontinent briefs, are provided comprising an absorbent article and having disposed thereon an effective amount of a particulate skin irritant sequestering agent. In an embodiment, the absorbent personal care article can further comprise a lipophilic skin health benefit agent. The particulate skin irritant sequestering agent comprises the magnesium aluminosilicate employed in the invention. Other clays (naturally occurring or synthetic), such as bentonite or laponite, can also be added to the composition of the invention, provided that the composition comprises the synthetic magnesium aluminosilicate clay described above.

As used herein, the term "sequestering agent" means a material that can adsorb a target molecule, such as a fecal protease, by covalent or non-covalent mechanisms. Body derived liquids, gases, and effluvia can have unpleasant odors. In addition, bacterially derived compounds, molecules, and proteins can also be present on or in the human body and cause unwanted odors. A sequestering agent can be used to absorb either bodily derived or bacterially derived odor causing substances. In certain embodiments, the affinity for the irritant is high, rapid, and irreversible. As used herein, the term "sequestration" is defined as the process of binding of an irritant to a sequestering agent, by covalent or non-covalent mechanisms.

The magnesium aluminosilicate clay described herein can act as a sequestering agent in a personal care composition such as a diaper or adult incontinence article. The adsorption of fecal proteases to sequestering agents minimizes their ability to penetrate into the skin and cause skin irritation. The sequestering agent may be of sufficient size or charge that precludes its penetration into the skin. Thus, any protease adsorbed to the surface of the sequestering agent would not be expected to act underneath the surface of the skin and cause skin damage and inflammation.

This benefit may also be realized by using materials within an absorbent structure that have sequestering agent(s) bound thereto. In this case, the benefit is realized by binding irritants to the absorbent structure itself. The binding of skin irritants to the materials of the absorbent structure will again afford skin health benefits. It will be apparent to the artisan that the two approaches of binding skin irritants to sequestering agents deposited on the skin or binding them to sequestering agents on the product are not mutually exclusive strategies.

In an embodiment, when the magnesium aluminosilicate clay acts as a sequestering agent in compositions of the present invention such as diapers and incontinence products, the magnesium aluminosilicate clay is not organophilically modified. As used herein, "organophilically modified" describes a compound which has been treated with long-chain organic amphiphilic compounds such as quaternary amines which results in exchange of the alkali metal ions by cationic organic molecules. Non-organophilically modified sequestering agents can include minor other processing modifications, such as the addition of inorganic counter ions, such as mono- and di-valent cations, e.g. lithium, sodium, calcium, or potassium.

Personal care, cosmetic, and pharmaceutical compositions of the invention can further comprise lipophilic skin health benefit agents. These agents include, but are not limited to, stearic acid, isoparrafin, petrolatum, and combinations thereof. The lipophilic skin health benefit agent can also be selected from fatty acids, fatty acid esters, fatty alcohols, triglycerides, phospholipids, mineral oils, essential oils, sterols, sterol esters, emollients, waxes, and combinations thereof. In some embodiments, the lipophilic skin health benefit agent has an average hydrocarbon chain with length greater than eight carbons (C-8).

As used herein, suitable lipophilic skin health benefit agents include, but are not limited to, the following materials classified according to CTFA designations:

1) Fats and Oils

Apricot Kernel Oil, Avocado Oil, Babassu Oil, Borage Seed Oil, Butter, $C_{12}$-$C_{18}$ Acid Triglyceride, Camellia Oil, Canola Oil, Caprylic/Capric/Lauric Triglyceride, Caprylic/Capric/Linoleic Triglyceride, Caprylic/Capric/Stearic Triglyceride, Caprylic/Capric Triglyceride, Carrot Oil, Cashew Nut Oil, Castor Oil, Cherry Pit Oil, Chia Oil, Cocoa Butter, Coconut Oil, Cod Liver Oil, Corn Germ Oil, Corn Oil, Cottonseed Oil, $C_{10}$-$C_{18}$ Triglycerides, Egg Oil, Epoxidized Soybean Oil, Evening Primrose Oil, Glyceryl Triacetyl Hydroxystearate, Glyceryl Triacetyl Ricinoleate, Glycosphingolipids, Grape Seed Oil, Hazelnut Oil, Human Placental Lipids, Hybrid Safflower Oil, Hybrid Sunflower Seed Oil, Hydrogenated Castor Oil, Hydrogenated Castor Oil Laurate, Hydrogenated Coconut Oil, Hydrogenated Cottonseed Oil, Hydrogenated $C_{12}$-$C_{18}$ Triglycerides, Hydrogenated Fish Oil, Hydrogenated Lard, Hydrogenated Menhaden Oil, Hydrogenated Mink Oil, Hydrogenated Orange Roughy Oil, Hydrogenated Palm Kernel Oil, Hydrogenated Palm Oil, Hydrogenated Peanut Oil, Hydrogenated Shark Liver Oil, Hydrogenated Soybean Oil, Hydrogenated Tallow, Hydrogenated Vegetable Oil, Lanolin and Lanolin Derivatives, Lard, Lauric/Palmitic/Oleic Triglyceride, Lesquerella Oil, Linseed Oil, Macadamia Nut Oil, Maleated Soybean Oil, Meadowfoam Seed Oil, Menhaden Oil, Mink Oil, Moringa Oil, Mortierella Oil, Neatsfoot Oil, Oleic/Linoleic Triglyceride, Oleic/Palmitic/Lauric/Myristic/Linoleic Triglyceride, Oleostearine, Olive Husk Oil, Olive Oil, Omental Lipids, Orange Roughy Oil, Palm Kernel Oil, Palm Oil, Peach Kernel Oil, Peanut Oil, Pengawar Djambi Oil, Pentadesma Butter, Phospholipids, Pistachio Nut Oil, Placental Lipids, Rapeseed Oil, Rice Bran Oil, Safflower Oil, Sesame Oil, Shark Liver Oil, Shea Butter, Soybean Oil, Sphingolipids, Sunflower Seed Oil, Sweet Almond Oil, Tall Oil, Tallow, Tribehenin, Tricaprin, Tricaprylin, Triheptanoin, Trihydroxymethoxystearin, Trihydroxystearin, Triisononanoin, Triisostearin, Trilaurin, Trilinolein, Trilinolenin, Trimyristin, Trioctanoin, Triolein, Tripalmitin, Trisebacin, Tristearin, Triundecanoin, Vegetable Oil, Walnut Oil, Wheat Bran Lipids, Wheat Germ Oil, Zadoary Oil, and the like, as well as mixtures thereof.

2) Fatty Acids

Arachidic Acid, Arachidonic Acid, Behenic Acid, Capric Acid, Caproic Acid, Caprylic Acid, Coconut Acid, Corn Acid, Cottonseed Acid, Hydrogenated Coconut Acid, Hydrogenated Menhaden Acid, Hydrogenated Tallow Acid, Hydroxystearic Acid, Isostearic Acid, Lauric Acid, Linoleic Acid, Linolenic Acid, Linseed Acid, Myristic Acid, Oleic Acid, Palmitic Acid, Palm Kernel Acid, Pelargonic Acid, Ricinoleic Acid, Soy Acid, Stearic Acid, Tall Oil Acid, Tallow Acid, Undecanoic Acid, Undecylenic Acid, Wheat Germ Acid, and the like, as well as mixtures thereof.

3) Fatty Alcohols

Behenyl Alcohol, $C_9$-$C_{11}$ Alcohols, $C_{12}$-$C_{13}$ Alcohols, $C_{12}$-$C_{15}$ Alcohols, $C_{12}$-$C_{16}$ Alcohols, $C_{14}$-$C_{15}$ Alcohols, Caprylic Alcohol, Cetearyl Alcohol, Cetyl Alcohol, Coconut Alcohol, Decyl Alcohol, Hydrogenated Tallow Alcohol, Lauryl Alcohol, Myristyl Alcohol, Oleyl Alcohol, Palm Alcohol, Palm Kernel Alcohol, Stearyl Alcohol, Tallow Alcohol, Tridecyl Alcohol, and the like, as well as mixtures thereof.

4) Essential Oils

Anise Oil, Balm Mint Oil, Basil Oil, Bee Balm Oil, Bergamot Oil, Birch Oil, Bitter Almond Oil, Bitter Orange Oil, Calendula Oil, California Nutmeg Oil, Caraway Oil, Cardamom Oil, Chamomile Oil, Cinnamon Oil, Clary Oil, Cloveleaf Oil, Clove Oil, Coriander Oil, Cypress Oil, Eucalyptus Oil, Fennel Oil, Gardenia Oil, Geranium Oil, Ginger Oil, Grapefruit Oil, Hops Oil, Hyptis Oil, Indigo Bush Oil, Jasmine Oil, Juniper Oil, Kiwi Oil, Laurel Oil, Lavender Oil, Lemongrass Oil, Lemon Oil, Linden Oil, Lovage Oil, Mandarin Orange Oil, Matricaria Oil, Musk Rose Oil, Nutmeg Oil, Olibanum, Orange Flower Oil, Orange Oil, Patchouli Oil, Pennyroyal Oil, Peppermint Oil, Pine Oil, Pine Tar Oil, Rose Hips Oil, Rosemary Oil, Rose Oil, Rue Oil, Sage Oil, Sambucus Oil, Sandalwood Oil, Sassafras Oil, Silver Fir Oil, Spearmint Oil, Sweet Marjoram Oil, Sweet Violet Oil, Tar Oil, Tea Tree Oil, Thyme Oil, Wild Mint Oil, Yarrow Oil, Ylang Ylang Oil, and the like, as well as mixtures thereof.

5) Sterol Derivatives

As used herein, suitable sterols and sterol derivatives include, but are not limited to, the following materials: sterols having a tail on the 17 position and having no polar groups for example cholesterol, sitosterol, stigmasterol, and ergosterol, as well as, $C_{10}$-$C_{30}$ cholesterol lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, avocadin, sterol esters, and the like, as well as mixtures thereof.

6) Emollients

As used herein, suitable emollients include, but are not limited to, the following materials: Mineral Oil, Mineral Jelly, Petrolatum, cosmetic esters, fatty esters, glyceryl esters, alkoxylated carboxylic acids, alkoxylated alcohols, fatty alcohols, lanolin and lanolin derivatives, petrolatum base oils, silicones, fats, hydrogenated vegetable oils, polyhydroxy esters, and the like, as well as mixtures thereof.

7) Waxes

As used herein, suitable waxes include, but are not limited to, the following materials: natural and synthetic waxes, such as bayberry wax, beeswax, $C_{30}$ alkyl dimethicone, candelila wax, carnuaba, ceresin, cetyl esters, hydrogenated cottonseed oil, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, motan acid wax, motan wax, ouricury wax, ozokerite, paraffin, PEG-6 beeswax, PEG-8 beeswax, rice bran wax, shellac wax, spent grain wax, steryl dimethicone synthetic beeswax, synthetic candelilla wax, synthetic camuba wax, synthetic japan wax. Synthetic jojoba wax, synthetic wax, and the like, as well as mixtures thereof. The preferred waxes include but are not limited to; carnuba, cerasin, cetyl esters, microcrystalline wax, montan wax, ozokerite, synthetic wax, and the like, as well as mixtures thereof.

8) Humectants

Humecants may also be included in the composition to provide an enhanced barrier and/or skin moisturization benefit. Humectants are typically cosmetic ingredients used to increase the water content of the top layers of the skin. This group of materials includes primarily hydroscopic ingredients. As used herein, suitable humectants include, but are not limited to, the following materials Acetamide MEA, Aloe Vera Gel, Arginine PCA, Chitosan PCA, Copper PCA, Corn Glycerides, Dimethyl Imidazolidinone, Fructose, Glucamine, Glucose, Glucose Glutamate, Glucuronic Acid, Glutamic Acid, Glycereth-7, Glycereth-12, Glycereth-20, Glycereth-26, Glycerin, Honey, Hydrogenated Honey, Hydrogenated Starch Hydrolysate, Hydrolyzed Corn Starch, Lactamide MEA, Lactic Acid, Lactose Lysine PCA, Mannitol, Methyl Gluceth-10, Methyl Gluceth-20, PCA, PEG-2 Lactamide, PEG-10 Propylene Glycol, Polyamino Sugar Condensate, Potassium PCA, Propylene Glycol, Propylene Glycol Citrate, Saccharide Hydrolysate, Saccharide Isomerate, Sodium Aspartate, Sodium Lactate, Sodium PCA, Sorbitol, TEA-Lactate, TEA-PCA, Urea, Xylitol, and the like, as well as mixtures thereof.

9) Surfactants

The composition may also include emulsifying surfactants. The surfactants include, but are not limited to, sorbitan monooleate, sorbitan sesquioleate, sorbitan trioleate, glyceryl stearate, sorbitan stearate, sorbitan tristearate, and the like, as well as mixtures thereof.

10) Viscosity Enhancers

The composition may also include viscosity enhancers. As used herein, suitable viscosity enhancers include, but are not limited to, the following materials: the group consisting of polyolefin resins, polyolefin polymers, ethylene/vinyl acetate copolymers, polyethylene, and the like, as well as mixtures thereof. Lipophilic skin health benefit agent lotion compositions can include humectants, surfactants, and viscosity enhancers present in an amount ranging from about 0.1% to about 10.0% of the total weight of the lipophilic skin health benefit agent composition.

It will be apparent to those skilled in the art that additional agents may be desirable for inclusion in the compositions described herein. Examples include, but are not limited to, acceptable carriers, anti-inflammatories, antimicrobials, antipuretics, skin protectants, buffering agents, α-hydroxy acids, microbial or algal extracts and/or fractions thereof, enzyme inhibitors, antihistamines, antioxidants, analgesics, antioxidants, astringents, fragrances, dyes, natural and/or synthetic vitamin analogs, sunscreens, deodorants, and combinations thereof. Further examples of which are given below.

In an embodiment, the invention is directed to a cosmetic composition comprising the magnesium aluminosilicate clay. The oil absorption capacity of the magnesium aluminosilicate clay employed in the invention can encourage the movement of the sebum into the intraparticle pores and interstices that are formed within the magnesium aluminosilicate clay. The high surface area of the magnesium aluminosilicate clay allows for the sebum to be easily adsorbed onto the surfaces of the clay particles. Thus, by incorporating the synthetic magnesium aluminosilicate clay into the cosmetic compositions, the resulting cosmetic compositions are more resistant to deterioration by sebum and provide more attractive, durable, long-lasting wear. The cosmetic composition can be in dry form, powder form, or fluid form. Indeed, the present magnesium aluminosilicate clay particles are particularly suitable for use in fluid cosmetic compositions such as cremes or lotions. Because of their small particle size, they can be easily incorporated into a creme or lotion without giving it a gritty, uncomfortable feeling when applied to the skin.

In another embodiment, the invention is directed to a personal care composition comprising the magnesium aluminosilicate clay described above for use as a deodorant or a component in a deodorant product. The magnesium aluminosilicate clay can be present at a concentration suitable to permit malodor neutralization from a person's skin. In an embodiment, the magnesium aluminosilicate clay exhibits a pH level sufficiently low as not to destabilize or alter the functionality of other ingredients present within the target finished cosmetic and/or deodorant formulations.

Personal care compositions of the invention for use as deodorants can contain other components in addition to the magnesium aluminosilicate clay described above. For example, antiperspirant salts possible as materials within the inventive personal care compositions include, without limitation, any aluminum astringent antiperspirant salt or aluminum and/or zirconium astringent complex can be employed herein. Salts useful as astringent antiperspirant salts or as components of astringent complexes include aluminum halides, aluminum hydroxy-halides, zirconyl oxyhalides, zirconyl hydroxy-halides, and mixtures of these materials.

Aluminum salts of this type include aluminum chloride and the aluminum hydroxyhalides having the general formula $Al_2(OH)_xQ_yXH_2O$ where Q is chlorine, bromine or iodine; where x is from about 2 to about 5, and x+y=about 6, and x and y do not need to be integers; and where X is from about 1 to about 6. Aluminum salts of this type can be prepared in the manner described more fully in U.S. Pat. No. 3,887,692 issued to Gilman on Jun. 3, 1975, and U.S. Pat. No. 3,904,741 issued to Jones and Rubino on Sep. 9, 1975.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_2\text{-}n_zB_z$$

wherein z may vary from about 0.9 to about 2 and need not be an integer, n is the valence of B, 2-nz is greater than or equal to 0, and B may be selected from the group consisting of halides, nitrate, sulfamate, sulfate, and mixtures thereof. Although only zirconium compounds are exemplified in this specification, it will be understood that other Group IVB metal compounds, including hafnium, can be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than zero groups per molecule.

The invention also includes in an embodiment a method of inhibiting body odor by applying to the skin an effective amount of a personal care composition comprising the synthetic magnesium aluminosilicate clay described above.

In an embodiment, the personal care compositions of the invention incorporating the magnesium aluminosilicate clay described above can be capable of providing effective odor neutralization and suppression. Magnesium aluminosilicate clays are believed to offer two measures to neutralize body malodors: they not only absorb the malodors themselves, but they also reduce the quantities of fatty acids that are part of the cause of the malodors. It is believed that such malodorous compounds are attracted into the intraparticle pores and interstices that are formed within the magnesium aluminosilicate clay. The molar composition of the magnesium aluminosilicate clay permits dissociation of metal cations and the silicate anion. Such freed metal cations (i.e. magnesium, sodium, calcium, etc.) can then react with the available anions (such as long-chain fatty acids, for instance isovaleric acid) of the targeted malodor-creating compounds to create low-volatility salts. As a result, such newly formed salts exhibit reduced volatility into the surrounding environment, and, ultimately, the chances of smelling such non-volatized compounds are drastically reduced if not prevented.

Personal care compositions prepared according to the present invention comprise about 0.5 wt % to about 99 wt %, preferably about 1 wt % to about 50 wt % of the magnesium aluminosilicate clay. In addition to the magnesium aluminosilicate clay, the present personal care compositions can also comprise one or more dermatologically acceptable cosmetic ingredients.

Dermatologically acceptable cosmetic ingredients include a diluent or carrier. The vehicle, diluent or carrier may be selected from a wide range of ingredients. The vehicle may comprise water and/or a water-miscible or dispersible organic liquid or liquids and alternatively or additionally a water-immiscible liquid or liquids and waxes. The cosmetically acceptable vehicle can form from 1% to 99% by weight of the composition, and can, in the absence of other cosmetic adjuncts, form the balance of the composition. The vehicle may be aqueous, non-aqueous or a combination of both, such as an emulsion. In a combination vehicle, an oil or oily material may be present, together with one or more emulsifiers to provide either a water-in-oil emulsion or an oil-in-water emulsion, depending largely on the average hydrophilic-lipophilic balance (HLB) of the emulsifiers employed. This also includes multiple emulsions: water-in-oil-in-water or oil-in-water-in-oil emulsions. For sebum absorption purposes, it is important that the magnesium aluminosilicate clay not be present within the oil phase of any emulsion since such magnesium aluminosilicate clays would be exhausted in terms of absorbing the oil portion of such a formulation prior to any chance of properly performing after application to a person's skin.

In the case where the composition contains a combination of aqueous and non-aqueous vehicle components, the aqueous phase can be from about 99 wt % to about 1 wt % of the vehicle, as can the non-aqueous phase.

In an embodiment of the invention where the vehicle is comprised of non-aqueous components, the dermatologically acceptable non-aqueous cosmetic ingredients in the vehicle will usually form from 1% to 99.5% by weight of the composition, preferably from 20% to 95%, and most preferably from 50% to 90% and may, in the absence of other cosmetic adjuncts, form the balance of the composition.

Examples of suitable non-aqueous carriers may include alcohols, polyalkoxylated glycols (such as propylene glycol), volatile and nonvolatile liquid silicone carriers (such as cyclicsilicone polymers), hydrocarbon and mineral oils and branched chain hydrocarbons. Specific, non-limiting examples of organic liquids suitable for use include octyldodecanol, butyl stearate, diisopropyl maleate, and combinations thereof. Also suitable for use are acrylic acid-based polymers.

In an embodiment, it can be desirable that the odor absorbing ingredient remains substantially localized in the region of the body to which it has been topically applied. In order to assist this to happen and also to enable alternative dispensers for the composition to be employed, the vehicle may be thickened or structured, for example by introducing one or more materials for that purpose. Thickened or structured compositions commonly adopt the form of firm sticks, soft solids and creams. In such circumstances, the materials are often referred to as structurants or gellants and may sometimes alternatively be called thickeners, depending on the final form of the composition. The vehicle may be further diluted with a volatile propellant and used as an aerosol; may be mixed with an additional liquid and/or other ingredients and used, for example, as a roll-on or squeeze-spray product; or mixed with one or more thickeners and/or structurants and used, for example, as a gel, soft solid, or solid stick product.

The personal care, cosmetic, and pharmaceutical compositions of the present invention may be prepared by any known or otherwise effective technique provided that the composition comprises the synthetic magnesium aluminosilicate described herein. Techniques for forming such compositions are very well known in the art. The present invention is not dependent upon any particular formulation technique, it being recognized that the choice of specific formulation components may well make necessary some specific formulation procedure.

Methods for preparing the personal care, cosmetic, and pharmaceutical compositions of the present invention include conventional formulation and mixing techniques. Many variations of formulating the compositions of the present invention exist, and all are considered within the scope of the present invention. For example, if the personal care composition is a deodorant, a suitable method includes combining the magnesium aluminosilicate clay with part or all of a liquid vehicle. A liquid may be entirely absorbed into the magnesium aluminosilicate clay, and if so, additional liquid or liquids and other materials are added until the magnesium aluminosilicate clay is evenly dispersed. A thickener or gellant is added and the composition is mixed and may be heated, if required for homogenous incorporation. Adjunct and/or additional materials may be added at this point, and the batch may be allowed to cool, if necessary. The thickened or gelled composition is allowed to become viscous or solidify in a suitable container or dispenser.

The fluid or solid personal care products prepared according to the present invention may also include other optional components. The CTFA Cosmetic Ingredient Handbook, Tenth Edition, 2004, which is incorporated by reference herein in its entirety, describes a wide variety of cosmetic and pharmaceutical ingredients commonly used in skin care compositions, and which are suitable for use in the compositions of the present invention. These optional components include pH buffering agents, additional malodor control agents, fragrance materials, dyes, and pigments, preservatives, skin aids (e.g., aloe), cosmetic astringents, liquid or solid emollients, emulsifiers, film formers, propellants, skin-conditioning agents, such as humectants, skin protectants, solvents, solubilizing agents, suspending agents, surfactants, waterproofing agents, viscosity increasing agents (aqueous and non-aqueous), waxes, wetting agents, and other optional components. Amounts of these adjunct components may range anywhere form 0.001% up to 20% by weight of the composition.

Slip compounds can be a component of the compositions of the invention of the present invention. Slip compounds include polyethylene; nylon; polytetra-fluoroethylene; silica which is in the form of microspheres, ellipsoids, barrel-shapes, and the like; mica, silicone (e.g. dimethicone) and metallic stearates (e.g. zinc stearate); and mixtures thereof. Additionally, some of the silica can be fumed silica for increased flowability of the powder in addition to enhancing the slip characteristics. When present in the compositions of the invention, the slip compounds can comprise from about 0.1% to about 35%, preferably from about 1% to about 10%, by weight of the composition.

The present invention may optionally also include dry or wet binders to help promote adhesion of the powder and active ingredients to the skin. Binders useful in the present invention are found in the Cosmetic Bench Reference, 1994 Edition, pages 13-14, which is incorporated herein by reference. Preferred binders are calcium stearate, zinc stearate, isopropyl myristate, magnesium myristate, silicone, and mixtures thereof. More preferred are zinc stearate, dimethicone, and mixtures thereof. When included in the composition, the binders are at a level of from about 0.1% to about 25%, preferably from about 1% to about 15%, by weight of the composition.

Anti-pruritic agents such as those known in the art may be included in the compositions of the present invention. Examples of anti-pruritic agents useful in the present invention are magnesium-L-lactate, hydrocortisone, hydrocortisone acetate, and colloidal oatmeal. A description of anti-pruritic agents are found in the Handbook of Non Prescription Drugs, 10th Edition, p. 529, 1993; which is incorporated herein by reference. When included in the composition, anti-pruritic agents may be present from about 0.1% to about 40%, by weight of the compositions.

Colorants and dyes can be optionally added to the cosmetic, personal care, and pharmaceutical compositions of the invention for visual appeal and performance impression. Colorants suitable for use in the present invention are found in the Cosmetic Bench Reference, 1994 Edition, pages 21-22, which is incorporated herein by reference.

Other dermatologically acceptable cosmetic ingredients include rheology affecting agents such as solidifying agents and gellants. The solidifying agents act to provide solidity to a personal care composition so that they are in solid (or semi-solid) form at room temperature. Suitable solidifying agents include especially high melting point waxes (melting points between 65° C.-110° C.) which include hydrogenated castor oil, paraffin, synthetic wax, ceresin, beeswax, and other such waxes. Also acceptable are low melting point waxes (melting points between 37° C.-65° C.), which include fatty alcohols, fatty acids, fatty acids esters, fatty acid amides, and the like.

Gellants are used in the case of solid stick compositions, to give the stick an appropriate consistency and provide an appropriate gel matrix and product hardness at the completion of processing. The gelling agents will vary depending on the particular form of the personal care composition and whether the personal care composition is aqueous or non-aqueous. Suitable gellants include esters and amides of fatty acid or hydroxy fatty acid gellants, fatty acid gellants, salts of fatty acids, esters and amides of fatty acid or hydroxy fatty acid gellants, cholesterolic materials, lanolinolic materials, fatty alcohols, triglycerides, substituted sorbitol acetal compounds, such as mono- and/or di-benzylidene sorbitols, such as, as one non-limiting example, 3,4-dimethylbenzylidene sorbitol, and other suitable solid, non-polymeric gellants. Preferred gellants (for both aqueous and nonaqueous compositions) include fatty alcohols, most preferably stearyl alcohol. Amounts of these gellant components may range anywhere from 0.001% up to 20% by weight of the composition.

The synthetic magnesium aluminosilicate clays employed in the invention can act as particulate based thickeners. In an embodiment, the magnesium aluminosilicate clay described above can be used alone or in combination as particulate gellants or thickeners for aqueous compositions, particularly oil-in-water (O/W) emulsions. Fundamentally, the formation of particulate gels is a manifestation of suspended colloidal particles forming a network structure that entraps and thus immobilizes the suspending medium. Clay-based gels may form when individual platelets or stacks of a few aggregated platelets (tactoids) engage in interparticle associations with their neighboring platelets. If these particle-to-particle links extend throughout the total available volume, a gel, comprised of a continuous, linked particulate structure that entraps within itself the suspending medium, is formed. Such interparticle associations are governed by the interplay between the attractive and repulsive forces that generally act between particles suspended in a liquid. Hydrodynamic effects due to the orientation of planar clay particles in a flow-field may also contribute to the rheological properties of clay suspensions.

In an embodiment, the personal care composition of the invention is a toothpaste. A toothpaste may be formulated to provide anti-caries and anti-plaque characteristics.

About 25% to about 35% by weight sorbitol may be added to water along with about 0.1% to about 0.5% of the magnesium aluminosilicate clay employed in the invention. The final amount of water in the formulation may be about 10% to about 50%. Silica may be added to the formulation at about 10% to about 30% by weight of water and the remainder of the formulation may include a fluoride compound for anti-caries activity, flavorings, and anti-bacterial, and anti-plaque additives. The fluoride compounds may include, but are not limited to sodium fluoride, potassium fluoride, sodium monofluorophosphate, and stannous fluoride. Antiplaque compounds may include, but are not limited to tetrasodium pyrophosphate or other soluble pyrophosphate compounds. Anti-bacterial toothpaste formulations may include compounds such as, but not limited to 2,4,4'-trichloro-2'-hydroxydiphenyl ether (Triclosan) or 2,2'-dihydroxy-5,5'-dibromodiphenyl ether. Additional information on formulations may be found in U.S. Pat. No. 5,525,330 to Gaffar, et al., which is incorporated herein by reference.

In an embodiment, the personal care composition of the invention is a sunscreen. The amount of magnesium aluminosilicate clay employed in the invention can range from 0.5 wt % to 50 wt %. The composition can further comprise particulate UVR-filter material, preferably in the range of about 1-65% by weight, based on the total weight of the composition. UVR-filters include, but are not limited to, titanium dioxide, zinc oxide, and metal oxides. In addition, the sunscreen composition optionally includes one or more of the following components: slip compounds, humectants, emollients, preservatives, whiteners, and the like.

The inventive compositions may contain any of a number of desired "active" ingredients, including drug substances such as anti-inflammatory agents, topical anesthetics, antimycotics, etc.; skin protectants or conditioners; humectants; and the like, depending on the intended uses for the formulations. In general, topical pharmaceutical compositions of the invention will comprise one or more active ingredients in addition to the synthetic magnesium aluminosilicate clay.

Other applications can be envisaged for the magnesium aluminosilicate clay such as their use as environmentally neutral constituents of detergents and cleaning preparations, more especially to their use as a builder constituent of low-phosphate and phosphate-free laundry detergents containing synthetic surfactants.

The magnesium aluminosilicate clay employed in the invention may be used as a Theological additive for aqueous compositions, including but not limited to, latex paints or drilling fluids. U.S. Pat. No. 5,164,433 to Ricci et al., which is incorporated herein by reference, provides further information regarding the use of clay as a rheological additive for aqueous systems.

The magnesium alumninosilicate clay employed in the invention may be formulated into a printing ink composition. A composition may include about 15 parts to about 25 parts soybean oil, about 15 parts to about 25 parts hydrocarbon oil, about 10 parts to about 20 parts asphaltic resin, about 5 parts to about 15 parts oil modified polyamide, about 0.5 parts to about 2.5 parts oxidized polyethylene, about 25 parts to about 45 parts carbon black, and about 0.1 parts to about 0.5 parts of the magnesium aluminosilicate clay. Addition of water to this composition may be desirable to produce an emulsified composition. This composition may produce a stable, high resistance to rub-off, printing ink. The components may be blended together in one step and mixed until the desired consistency may be achieved. Other compositions for printing inks may be found in U.S. Pat. No. 5,981,625 to Zou, et al., which is incorporated herein by reference.

An oven cleaner may be formulated with the magnesium aluminosilicate clay employed in the invention. In an embodiment, an oven cleaner may include, but is not limited to the following composition: water, the magnesium aluminosilicate clay, polymer, solvent, alkali metal hydroxide, and tetrapotassium pyrophosphate. In an embodiment, about 2% of the the magnesium aluminosilicate clay may be dispersed in sufficient water to provide a final water content in the formulation of about 30% to about 50%. Tetrapotassium pyrophosphate may be added at about 0.05% to about 0.15% prior to adding the selected smectite. About 10% to about 25% alkali metal hydroxide may be added after the selected smectite has hydrated. Other components may be added as desired, such as but not limited to, surfactants, solvents, and fragrances. Further formulations and details may be found in U.S. Pat. No. 3,779,933 to Eisen and U.S. Pat. No. 5,919,312 to Wierenga et al., both of which are incorporated herein by reference.

A glass cleaner may be formulated with the magnesium aluminosilicate clay, as described herein, to produce a non-drip glass cleaner. In an embodiment, about 0.5% to about 1.5% of the magnesium aluminosilicate clay may be dispersed in water. About 2% to about 10% of an alcohol may be added to the magnesium aluminosilicate clay dispersion. Examples of an alcohol may include, but are not limited to methanol, ethanol, 1-propanol, isopropanol, and butanol. An oil emulsifier may be added at about 0.5% to about 10% by weight of the formulation. An example of an oil emulsifier may include, but is not limited to an ammonia solution, butoxyethanol, propylene glycol, ethylene glycol, ethylene glycol polymers, polyethylene, or methoxypolyethylene glycols. A surfactant may be added to the formulation at about 0.1% to about 1% by weight. This formulation may provide a non-drip, streak-free composition for surface and glass cleaning. Other formulations may be found in U.S. Pat. No. 5,798,324 to Svoboda, which is incorporated herein by reference.

In an embodiment, the magnesium aluminosilicate clay may be mixed with a polymerizable organic system to produce nanocomposites. The the magnesium aluminosilicate clay may be compounded into a resin of choice using a twin-screw extruder, but other methods of mixing and extrusion may be used. The magnesium aluminosilicate clay may also be mixed with a monomer prior to polymerization. When polymerization commences, the magnesium aluminosilicate clay may be incorporated into the produced polymer. The polymer may then be processed further to form pellets, prills, fibers or such forms which may be used in further processing steps. Examples of further processing steps may include film production, thermoforming, blow molding or injection molding.

The magnesium aluminosilicate clay, herein described and employed in the invention, may be mixed with other polymerizable organic materials to produce a number of different products or articles. The magnesium aluminosilicate clay may be mixed with the polymerizable organic materials in automobile tires. The magnesium aluminosilicate clay may be added to impart improved performance of the automobile tire.

The magnesium aluminosilicate clay employed in the invention can be used as a carrier, an absorbent, or a filler. The magnesioum aluminosilicate clay can be incorporated as a dried solid in paints, rubber and paper, and in other materials such as agricultural goods by means known to the art. For example, the magnesium aluminosilicate clay can act as a carrier or drying agent for oils and chemicals. A composition can contain about 25 to 40 wt % of the magnesium aluminosilicate clay and about 60 to 75 wt % of the oil or chemical. This provides a semi-pasty product with most oils and liquid chemicals. While the physical form of such compositions varies with the characteristics, the magnesium aluminosilicate clay employed in the invention will usually absorb sufficient oil at 60 to 75% oil loadings to produce a resulting composition which is a dry, flowable powder. Thus the magnesium aluminosilicate clay employed in the invention has characteristics as a carrier, absorbent, and/or drying agent.

EXAMPLE

Example 1

A magnesium aluminosilicate clay with an elemental composition Mg5.4[Si 6.6 Al 1.4] O 20 (OH)4 with a Si/Al=4.7 was prepared as follows. Water glass (27 wt % $SiO_2$) was mixed with aluminum nitrate at room temperature and the pH adjusted to about 1 with nitric acid. A solution of magnesium nitrate was added to form a first reaction mixture. The pH of the first reaction mixture was then adjusted to about 8.4 with the addition of NaOH to form a second reaction mixture and the second reaction mixture was heated to 50° C. The reaction was allowed to proceed for 1 hour at 50° C. after which time the second reaction mixture was filtered and washed. The filtrate was a magnesium aluminosilicate clay of the invention.

Example 2

The magnesium aluminosilicate clay of Example 1 was added to a 0.1 M solution of ammonium nitrate to exchange the sodium cations for ammonium cations. The ammonium substituted magnesium aluminosilicate clay was collected by filtration and washed with water. The ammonium substituted magnesium aluminosilicate clay was then calcined at 450° C. degrees for 12 hours.

Example 3

The magnesium aluminosilicate clay of Example 2 was characterized by nitrogen adsorption/desorption. The surface area of the magnesium aluminosilicate was approximately 550 m2/g and the pore volume was approximately 0.9 cc/g. Mesoporosity of the material was confirmed by nitrogen adsorption/desorption hysteresis which was indicative of a mesoporous material.

Example 4

The magnesium aluminosilicate clay of Example 2 was characterized by transmission electron microscopy (TEM). Clay platelets were approximately 5 nm to 50 nm.

The invention claimed is:

1. A cosmetic composition comprising a magnesium aluminosilicate clay wherein said magnesium aluminosilicate clay is synthesized according to a method consisting essentially of the following steps:
   a) combining (1) a silicon component, (2) an aluminum component, and (3) a magnesium component, under aqueous conditions at ambient temperature and at ambient pressure, to form a first reaction mixture, wherein the pH of said first reaction mixture is acidic, the pH in the range between about 0 and about 5;
   b) adding an alkali base to the first reaction mixture to form a second reaction mixture wherein the pH of the second reaction mixture is greater than 7.5; and
   c) reacting the second reaction mixture for about one hour or less to form a product comprising a magnesium aluminosilicate clay.

2. The cosmetic composition of claim 1, further comprising at least one skin aid selected from the group consisting of skin protectants, diluents, lipophilic skin health benefit agents, sunscreens, humectants, emollients, slip compounds, and moisturizers.

3. The cosmetic composition of claim 1, further comprising a pigment.

4. The composition of claim 1, wherein the magnesium aluminosilicate clay has a silicon to aluminum elemental mole ratio greater than 3 and wherein the $^{29}$Si NMR of the magnesium aluminosilicate clay comprises the following peaks

| Peaks | Chemical shift (ppm)[1] |
|---|---|
| P1 | −79 |
| P2 | −82 |
| P3 | −85 |
| P4 | −88 |
| P5 | −93. |

[1] +/− 3 ppm

5. The composition of claim 1, wherein the magnesium aluminosilicate clay is from 1% to 99% of the composition.

6. The composition of claim 1, wherein the magnesium aluminosilicate clay has a platelet size from 5 nm to 50 nm.

7. The composition of claim 1, wherein the magnesium aluminosilicate clay is mesoporous.

8. The composition of claim 1, wherein the magnesium aluminosilicate clay has a degree of stacking less than 10.

9. A personal care composition comprising a magnesium aluminosilicate clay wherein said magnesium aluminosilicate clay is synthesized according to a method consisting essentially of the following steps:
   a) combining (1) a silicon component, (2) an aluminum component, and (3) a magnesium component, under aqueous conditions at ambient temperature and at ambient pressure, to form a first reaction mixture, wherein the pH of said first reaction mixture is acidic, the pH in the range between about 0 and about 5;
b) adding an alkali base to the first reaction mixture to form a second reaction mixture wherein the pH of the second reaction mixture is greater than 7.5; and
c) reacting the second reaction mixture for about one hour or less to form a product comprising a magnesium aluminosilicate clay.

10. The personal care composition of claim 9, further comprising at least one odor controlling agent selected from the group consisting of zeolites, activated charcoal, sodium bicarbonate, antimicrobial agents, and antiperspirants.

11. The composition of claim 9, wherein the magnesium aluminosilicate clay has a silicon to aluminum elemental mole ratio greater than 3 and wherein the $^{29}$Si NMR of the magnesium aluminosilicate clay comprises the following peaks

| Peaks | Chemical shift (ppm)[1] |
|---|---|
| P1 | −79 |
| P2 | −82 |
| P3 | −85 |
| P4 | −88 |
| P5 | −93. |

[1] +/− 3 ppm

12. The composition of claim 9, wherein the magnesium aluminosilicate clay is from 1% to 99% of the composition.

13. The composition of claim 9, wherein the magnesium aluminosilicate clay has a platelet size from 5 nm to 50 nm.

14. The composition of claim 9, wherein the magnesium aluminosilicate clay is mesoporous.

15. The composition of claim 9, wherein the magnesium aluminosilicate clay has a degree of stacking less than 10.

16. A method of absorbing an odor-causing substances comprising contacting the odor-causing substance with the composition of claim 10.

17. The method of claim 16, wherein the odor-causing substance comprises body derived fluids, body derived effluvia, or combinations thereof.

18. The method of claim 16, wherein the odor-causing substance comprises bacterially derived compounds, proteins, or combinations thereof.

* * * * *